United States Patent
Cai et al.

[11] Patent Number: 6,051,022
[45] Date of Patent: Apr. 18, 2000

[54] BILEAFLET VALVE HAVING NON-PARALLEL PIVOT AXES

[75] Inventors: Qingsheng Cai; Yi-Ren Woo, both of Woodbury, Minn.

[73] Assignee: St. Jude Medical, Inc., St. Paul, Minn.

[21] Appl. No.: 09/224,239

[22] Filed: Dec. 30, 1998

[51] Int. Cl.[7] .................................................. A61F 2/24
[52] U.S. Cl. ................................................................ 623/2
[58] Field of Search ........................................ 623/2, 900

[56] References Cited

U.S. PATENT DOCUMENTS

| | | |
|---|---|---|
| 3,861,416 | 1/1975 | Wichterle . |
| 3,938,197 | 2/1976 | Milo . |
| 4,078,268 | 3/1978 | Possis . |
| 4,114,202 | 9/1978 | Roy et al. . |
| 4,406,022 | 9/1983 | Roy . |
| 4,484,365 | 11/1984 | Murguet et al. ............................ 623/2 |
| 4,599,081 | 7/1986 | Cohen ........................................ 623/2 |
| 4,676,789 | 6/1987 | Sorensen et al. .......................... 623/2 |
| 4,820,299 | 4/1989 | Philippe et al. ........................... 623/2 |
| 4,863,458 | 9/1989 | Bokros ....................................... 623/2 |
| 4,888,009 | 12/1989 | Lederman et al. ......................... 623/2 |
| 4,888,010 | 12/1989 | Bokros ...................................... 623/2 |
| 5,078,739 | 1/1992 | Martin ....................................... 623/2 |
| 5,123,918 | 6/1992 | Perrier et al. ............................. 623/2 |
| 5,207,707 | 5/1993 | Gourley ..................................... 623/2 |
| 5,314,467 | 5/1994 | Shu ........................................... 623/2 |
| 5,522,886 | 6/1996 | Milo .......................................... 623/2 |
| 5,628,791 | 5/1997 | Bokros et al. ............................. 623/2 |
| 5,628,792 | 5/1997 | Lentell ...................................... 623/2 |

*Primary Examiner*—David H. Willse
*Attorney, Agent, or Firm*—Hallie A. Finucane, Esq.; Westman, Champlin & Kelly, P.A.

[57] ABSTRACT

A bileaflet heart valve prosthesis includes an orifice body or housing defining an orifice or opening for the passage of blood therethrough. First and second leaflets or occluders are disposed in the orifice and pivotally attached to the orifice body. The first and second occluders pivot about axes between an open position and a closed position, and the axes are non-parallel. The orifice is substantially open when the first and second occluders are in their open positions and substantially closed when the occluders are in their closed position. The bileaflet heart valve may be either a central opening valve, or a side opening valve.

33 Claims, 10 Drawing Sheets

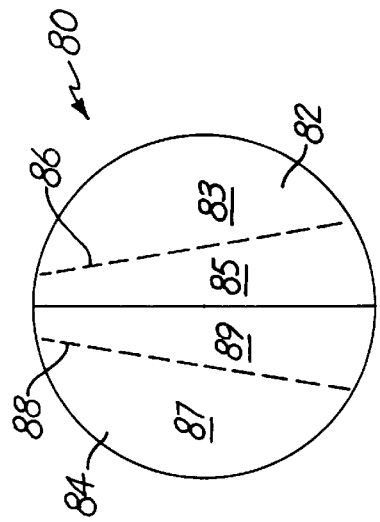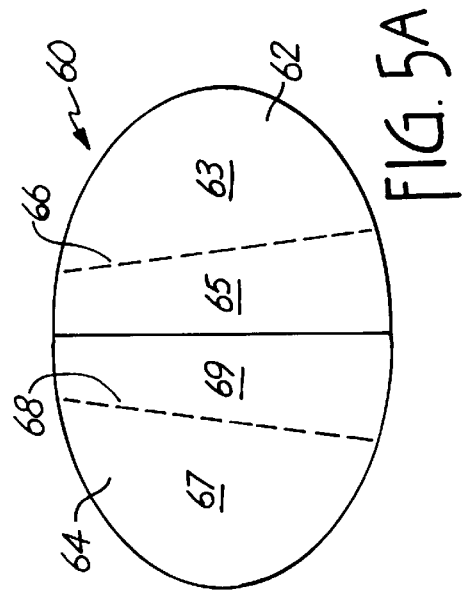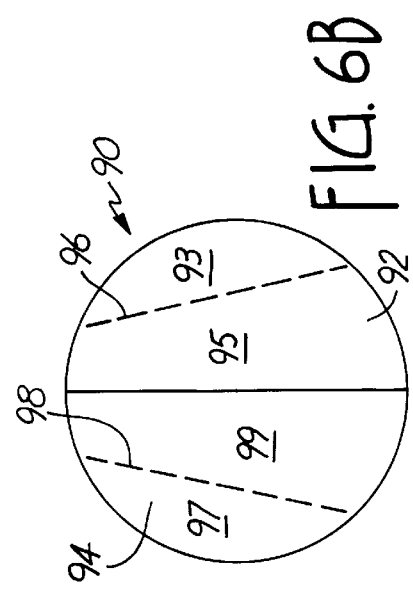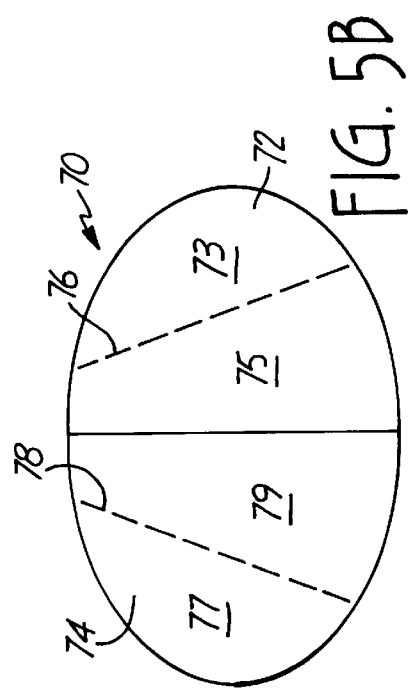

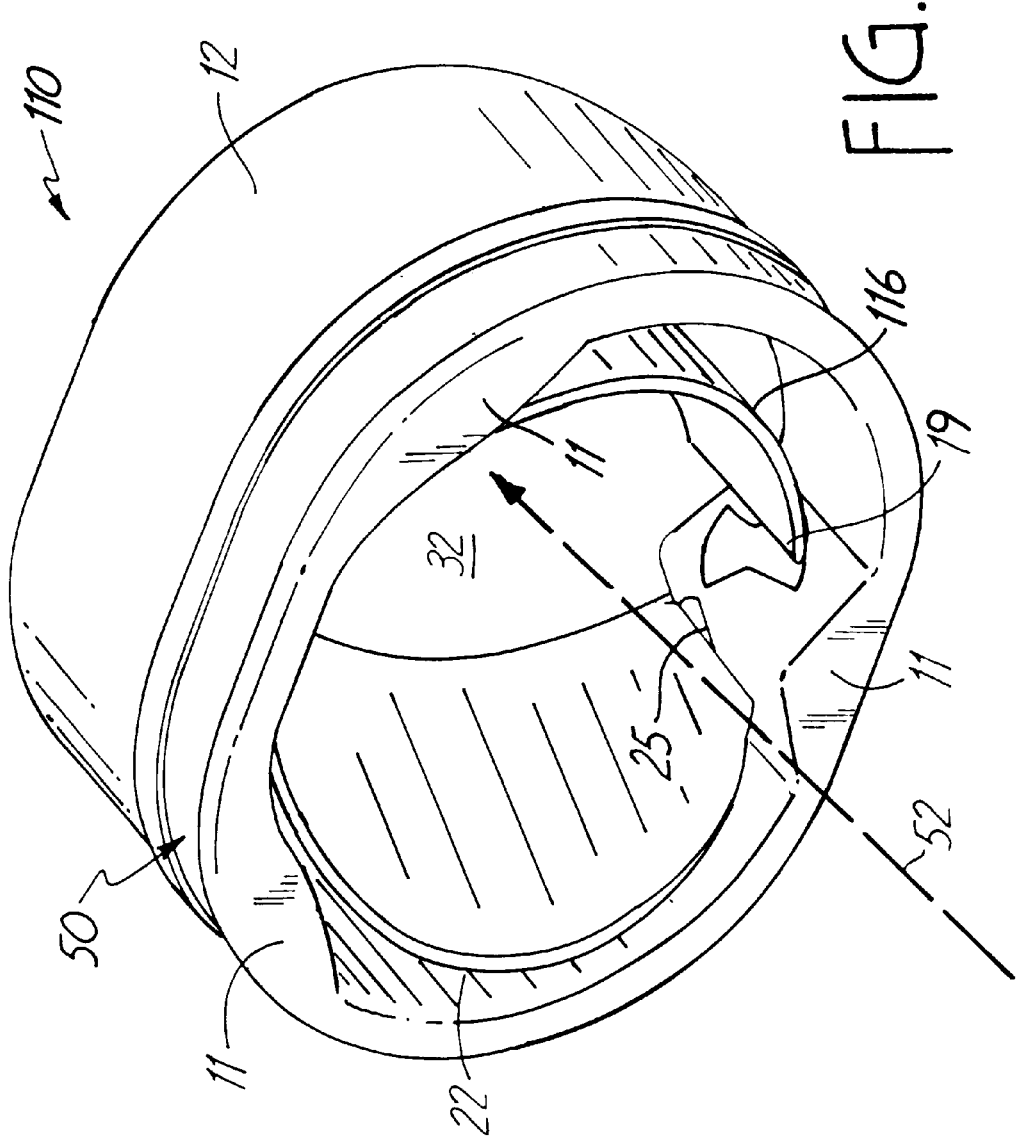

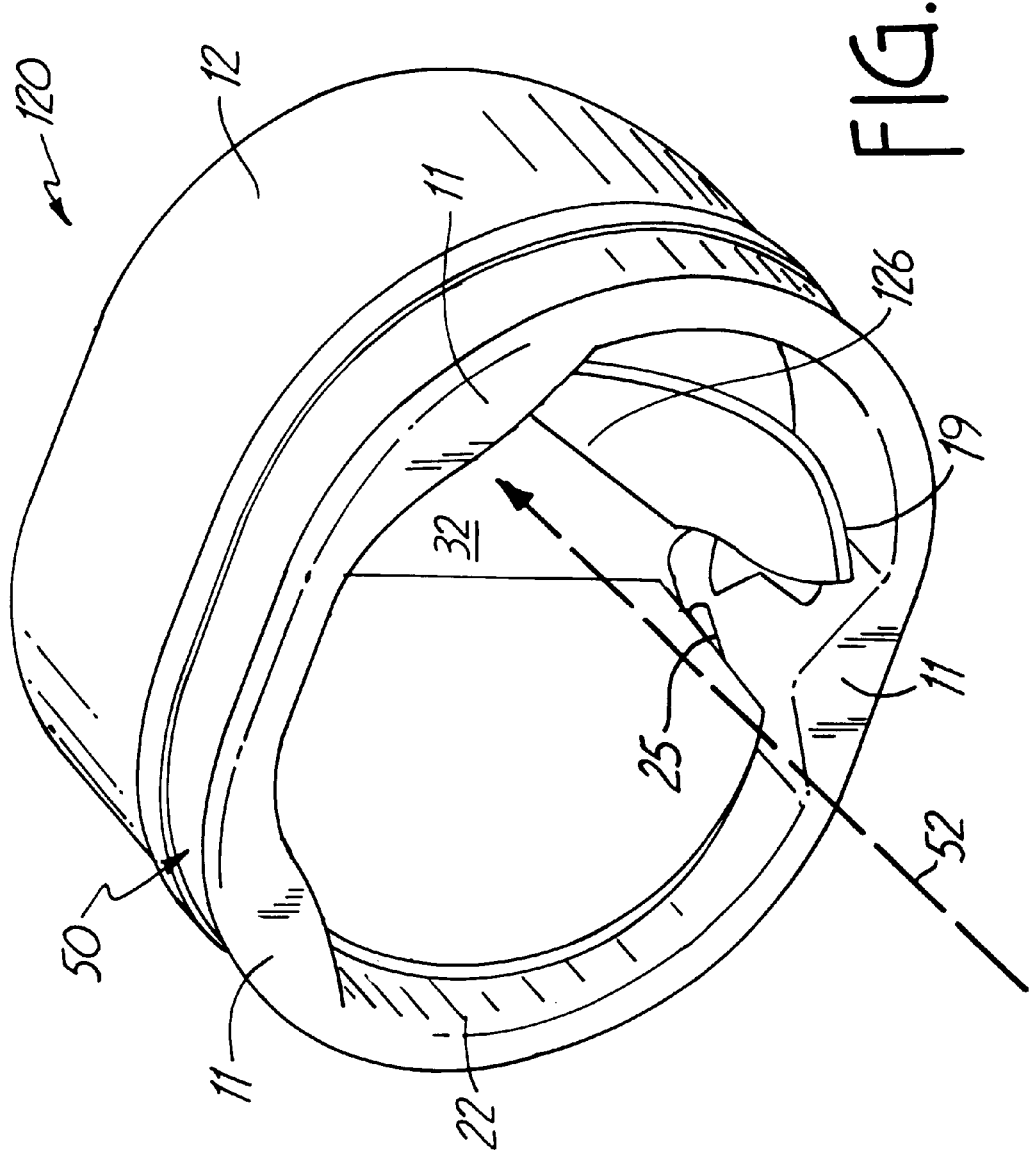

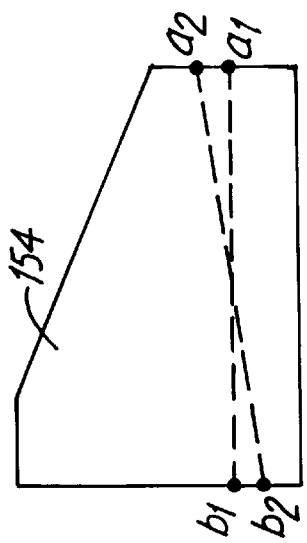
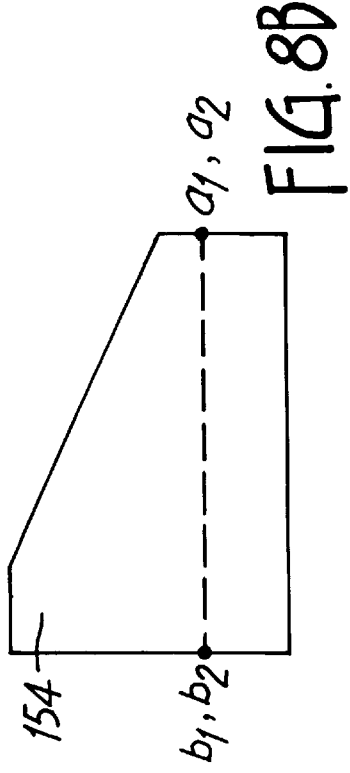
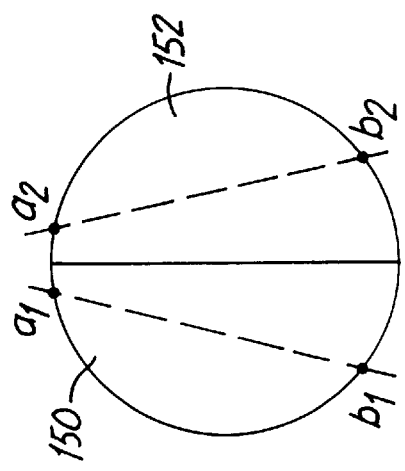
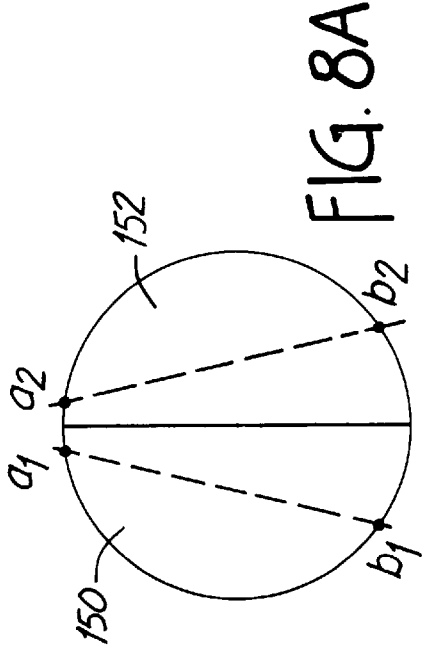

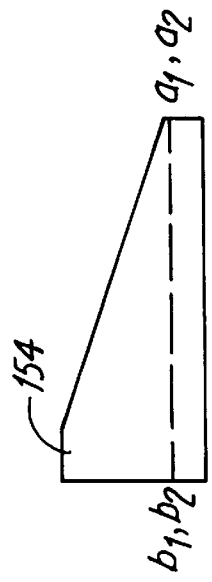
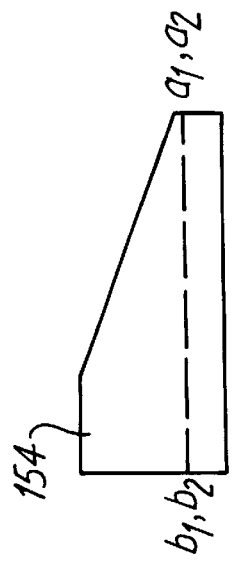
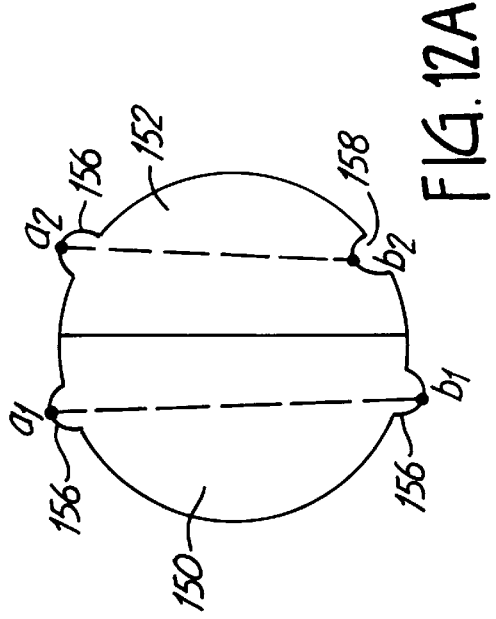
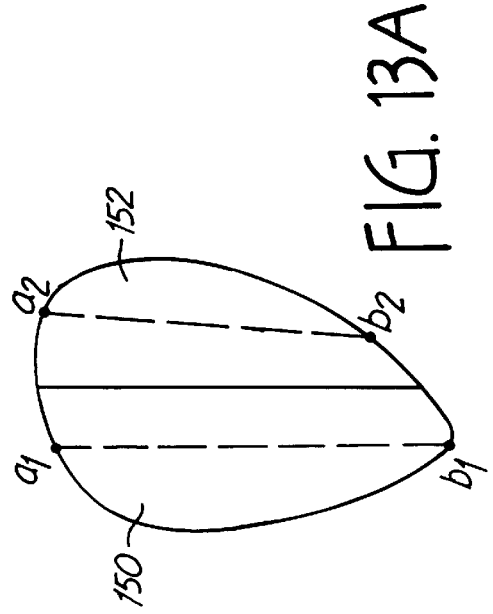

BILEAFLET VALVE HAVING NON-PARALLEL PIVOT AXES

BACKGROUND OF THE INVENTION

The present invention generally relates to mechanical heart valve prostheses. More specifically, the present invention relates to improved bileaflet mechanical heart valve prostheses.

Prosthetic valves are utilized to replace malformed, damaged, diseased or otherwise malfunctioning valves in body passageways, such as heart valves including the tricuspid valve, the bicuspid or mitral valve, the aortic valve and the pulmonary valve. Such prosthetic heart valves are typically implanted into the heart either by open chest surgery which requires a sternotomy or by minimally invasive surgery which requires a thoracotomy between adjacent ribs.

Heart valve prostheses may be divided into two groups, namely tissue valves and mechanical valves. Prosthetic tissue valves are harvested from a suitable animal heart, usually a porcine heart, prepared according to known methods, and may be mounted to a stent to facilitate implantation. Mechanical valves, by contrast, utilize a synthetic valve having a ball, a disc, a pair of leaflets or occluders (bileaflet), or a plurality of leaflets to regulate blood flow therethrough.

A mechanical heart valve prosthesis is optimally designed to perform the same functions as a healthy native valve under the same operating conditions. In particular, a mechanical heart valve is designed to regulate blood flow into and out of the heart chambers. Mechanical heart valves permit blood flow in only one direction and are actuated between an open position and a closed position by the changing hemodynamic conditions of the heart—i.e., by changes in blood flow and pressure caused by the pumping action of the heart.

Ideally, a mechanical heart valve prosthesis imposes no more resistance to blood flow than a healthy native heart valve. However, mechanical valves typically have less efficient flow and may be more thrombogenic than healthy native valves. The inefficient flow may be caused by design limitations associated with the relatively small orifice, the profile or shape of the leaflets and the dynamic movement of the leaflets. The potential consequence is a high pressure drop and/or turbulent flow across the valve. The thrombogenic nature is usually due to the valve geometry which may include stagnation points and the valve material which may have some inherent thrombogenic properties. The dynamic movement of the leaflets at valve closing generates a high impact force which damages the blood elements and further contributes to the thrombogenicity of a valve design. Improvements in blood flow efficiency and thrombogenic resistance are desirable to more closely simulate a healthy native valve.

As stated previously, inefficient flow in mechanical heart valves may be caused by the relatively small orifice—i.e., the relatively small opening through which blood flows when the valve is in the open position. The size of the orifice is limited by the space consumed by the sewing or suture ring (cuff) and the valve housing. The suture ring is necessary to facilitate mounting the valve in the heart and the valve housing is necessary to support the occluders.

The valve housing typically defines a flow orifice(s). In a bileaflet valve design, two opposing flat portions are typically utilized to accommodate the hinge points, with two hinge points associated with each flat portion. The two flat portions consume additional space that might otherwise define the orifice opening and accommodate more blood flow. It is desirable, therefore, to minimize the effect of the flat portions in a bileaflet valve design in order to improve the efficiency of the valve.

Also in a bileaflet design, it is desirable to maximize the size of the central opening—i.e., the opening between the two leaflets when the leaflets are in the open position. Maximizing the central opening reduces drag caused by the leaflets and improves blood flow in the center of the lumen which is typically the high velocity and high fluid stress region. One approach to increase the size of the central opening is by spacing the axes of the leaflets further apart. This typically requires an enlargement of the flat portions on the housing to accommodate the distance between the pivot axes. Increasing the size of the flat portions is undesirable because the flow area is reduced, as discussed previously. Accordingly, it is desirable to increase the size of the central opening in a bileaflet valve, without sacrificing the efficiency in utilizing the total orifice area. Another consideration in a mechanical heart valve design is the dynamic movement of the leaflets at valve closing. A lower leaflet closing velocity (soft closing) is desirable because it generates a lower closing impact force and minimizes damage to blood elements.

SUMMARY OF THE INVENTION

The present invention satisfies the desire to increase the size of the central opening while maintaining an efficient use of the orifice area. In particular, the bileaflet heart valve prosthesis of the present invention provides a larger central opening and soft closing by utilizing two leaflets having non-parallel axes of rotation.

In one embodiment of the present invention, a bileaflet heart valve prosthesis includes an orifice body or housing defining an orifice or opening for the passage of blood therethrough. First and second leaflets or occluders are disposed in the orifice and are pivotally attached to the orifice body. The first and second leaflets pivot about axes between an open position and a closed position, and the axes are non-parallel. The orifice is substantially open when the first and second leaflets are in their open positions and substantially closed when the leaflets are in their closed position. The bileaflet heart valve may be either a central opening valve or a side opening valve.

BRIEF DESCRIPTION OF THE DRAWINGS

FIG. 5A is a schematic illustration of a side opening oval bileaflet heart valve in the closed position in accordance with another embodiment of the present invention.

FIG. 5B is a schematic illustration of a central opening oval bileaflet heart valve in the closed position in accordance with yet another embodiment of the present invention.

FIG. 6A is a schematic illustration of a side opening circular bileaflet heart valve in the closed position in accordance with a further embodiment of the present invention.

FIG. 6B is a schematic illustration of a central opening circular bileaflet heart valve in the closed position in accordance with yet a further embodiment of the present invention.

FIG. 7A is a perspective view of a bileaflet heart valve with leaflets having a concave curvature in accordance with another embodiment of the present invention.

FIG. 7B is a perspective view of a bileaflet heart valve with leaflets having composite curvature in accordance with another embodiment of the present invention.

FIG. 8A is a top plan view and

FIG. 8B is a side plan view of a valve illustrating an arrangement of pivot axes in accordance with one embodiment.

FIG. 9A is a top plan view and

FIG. 9B is a side plan view of a valve illustrating an arrangement of pivot axes in accordance with one embodiment.

FIG. 12A is a top plan view and

FIG. 12B is a side plan view of a valve illustrating an arrangement of pivot axes in accordance with one embodiment.

FIG. 13A is a top plan view and

FIG. 13B is a side plan view of a valve illustrating an arrangement of pivot axes in accordance with one embodiment.

DETAILED DESCRIPTION OF THE PREFERRED EMBODIMENTS

The following detailed description of the invention should be read with reference to the drawings, which are not necessarily to scale, in which similar elements are numbered the same. The detailed description and drawings depict selected preferred embodiments and are not intended to limit the scope of the invention.

Figure 1:
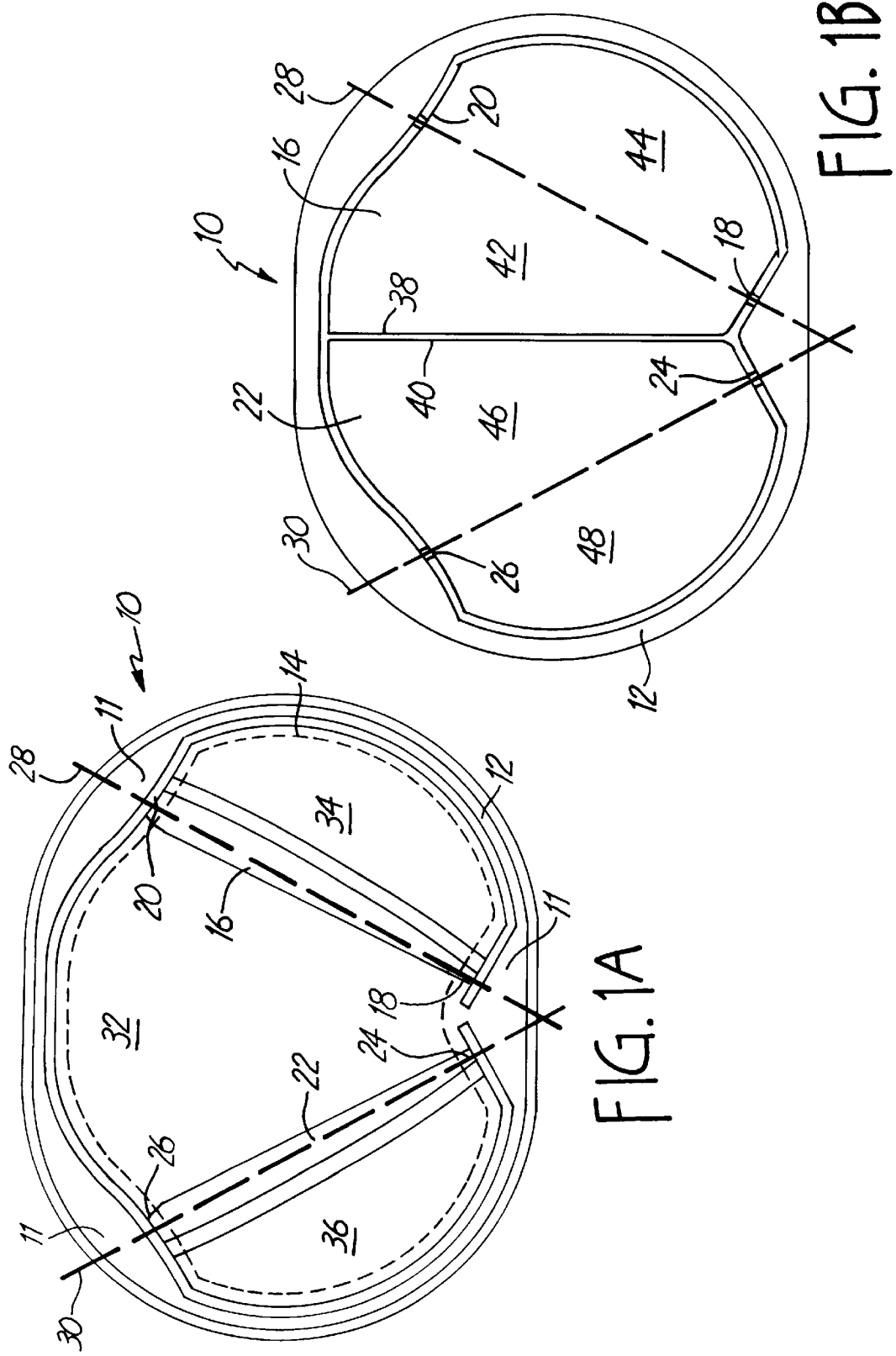
FIG. 1A is a bottom plan view of a bileaflet heart valve in the open position from the inflow side according to one embodiment of the present invention.
FIG. 1B is a bottom plan view of the bileaflet heart valve as in FIG. 1A, but in the closed position.

FIG. 1A illustrates a bileaflet heart valve 10 from an inflow side in the open position according to one embodiment of the present invention. The heart valve 10 includes an orifice body or housing 12 that defines an orifice 14. Although an oval orifice 14 is illustrated, other geometries may be employed, depending on the anatomical geometry that the valve 10 will be implanted into. For example, the orifice 14 may be circular, oval, D-shaped, or other non-circular shapes. In addition, the orifice 14 may be symmetrical or asymmetrical.

Figure 7C:
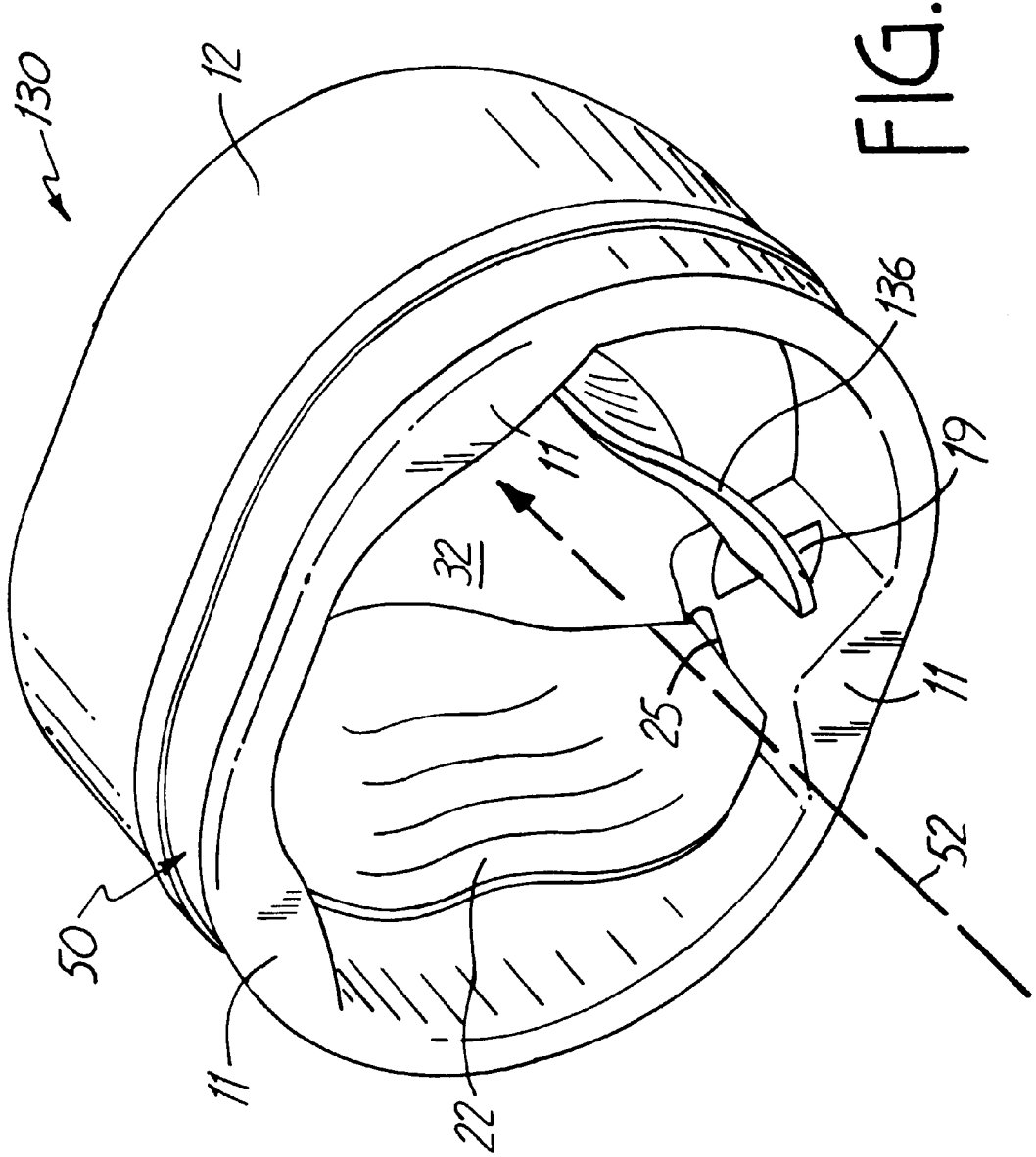
FIG. 7C is a perspective view of a bileaflet heart valve with leaflets having three dimensional composite curvature in accordance with another embodiment of the present invention.

A first leaflet or occluder 16 is disposed in the orifice 14 and is pivotally mounted to the interior of the housing 12 at pivot points 18 and 20. Similarly, a second leaflet or occluder 22 is disposed in the orifice 14 opposite first leaflet 16 and is pivotally mounted to the interior of the housing 12 at pivot points 24 and 26. The pivot points 18, 20, 24, 26 are on the interior surface of the housing 12. The first 16 and second 22 leaflets are preferably planar, but may also be curved as illustrated in FIGS. 7A, 7B and 7C. For purposes of illustration only, leaflets 16 and 22 are shown as planar or straight leaflets in all other figures.

The first leaflet 16 is movable between an open position and a closed position about axis 28. Similarly, the second leaflet 22 is movable between an open position and a closed position about axis 30. The first axis 28 and the second axis 30 are non-parallel, which provides a number of benefits to be described in detail hereinafter. The first 16 and second 22 leaflets, when in the open position, divide the orifice 14 into a central opening 32 and two side openings 34 and 36. Central opening 32 is preferably larger than either of the side openings 34 or 36 to permit the largest volume of blood to flow through the center of the orifice 14, which is typically the high flow region. A large central opening 32 maximizes the flow efficiency of the valve 10. However, the central opening 32 may be smaller than either of the side openings 34 or 36 if it is desirable to have a higher volume of blood flow through the side openings 34,36.

The angle between axes 28 and 30 projected onto a plane perpendicular to the blood flow direction 52 may be between approximately 1–179 degrees, preferably 10–95 degrees, and most preferably 20–60 degrees. The angle may be varied depending on the desired balance of the leaflets 16 and 22 and the desired size of the center opening 32. Further, each leaflet axis could be at a different angle relative to where the leaflets meet at edges 38,40, i.e., one at 15°, one at 25°. The distance between pivot points 18 and 24 is preferably less than the distance between pivot points 20 and 26. If the leaflets are curved or asymmetrical, these distances may be different and still provide for non-parallel axes 28 and 30. In all instances, the pivot points 18, 20, 24 and 26 define four corners of a polygon which approximates the central opening 32. The distance between pivot points 18 and 20 can be, but need not be, equal to the distance between pivot points 24 and 26.

When both the first 16 and the second 22 leaflets are in the closed position, the orifice 14 is closed as best illustrated in FIG. 1B. FIG. 1B is a bottom view of the bileaflet heart valve 10 from the inflow side as in FIG. 1A, but in the closed position. When in the closed position, the first 16 and second 22 leaflets are adjacent at edges 38 and 40, respectively. The perimeter of the leaflets 16 and 22 preferably establishes a substantially fluid tight seal with the inside surface of the housing 12. The edges 38 and 40 also preferably establish a substantially fluid tight seal when the valve 10 is in the closed position. The gap around the perimeter of the leaflets 16 and 22 and edges 38,40 is merely shown for purposes of clarity.

The first leaflet 16 is divided by first axis 28 into a first central portion 42 and a first side portion 44. Similarly, the second leaflet 22 is divided by second axis 30 into a second central portion 46 and a second side portion 48. The first 42 and second 46 central portions are preferably larger than the first 44 and second 48 side portions such that the first 42 and second 46 central portions move in the direction of flow. Alternatively, the first 42 and second 46 central portions may be smaller than the first 44 and second 48 side portions such that the first 44 and second 48 side portions move in the direction of flow. In the first embodiment, wherein the first 42 and second 46 central portions move in the direction of flow, valve 10 may be referred to as a central opening valve. In the second case, wherein the first 44 and second 48 side portions move in the direction of flow, valve 10 may be referred to as a side opening valve.

Figure 2:
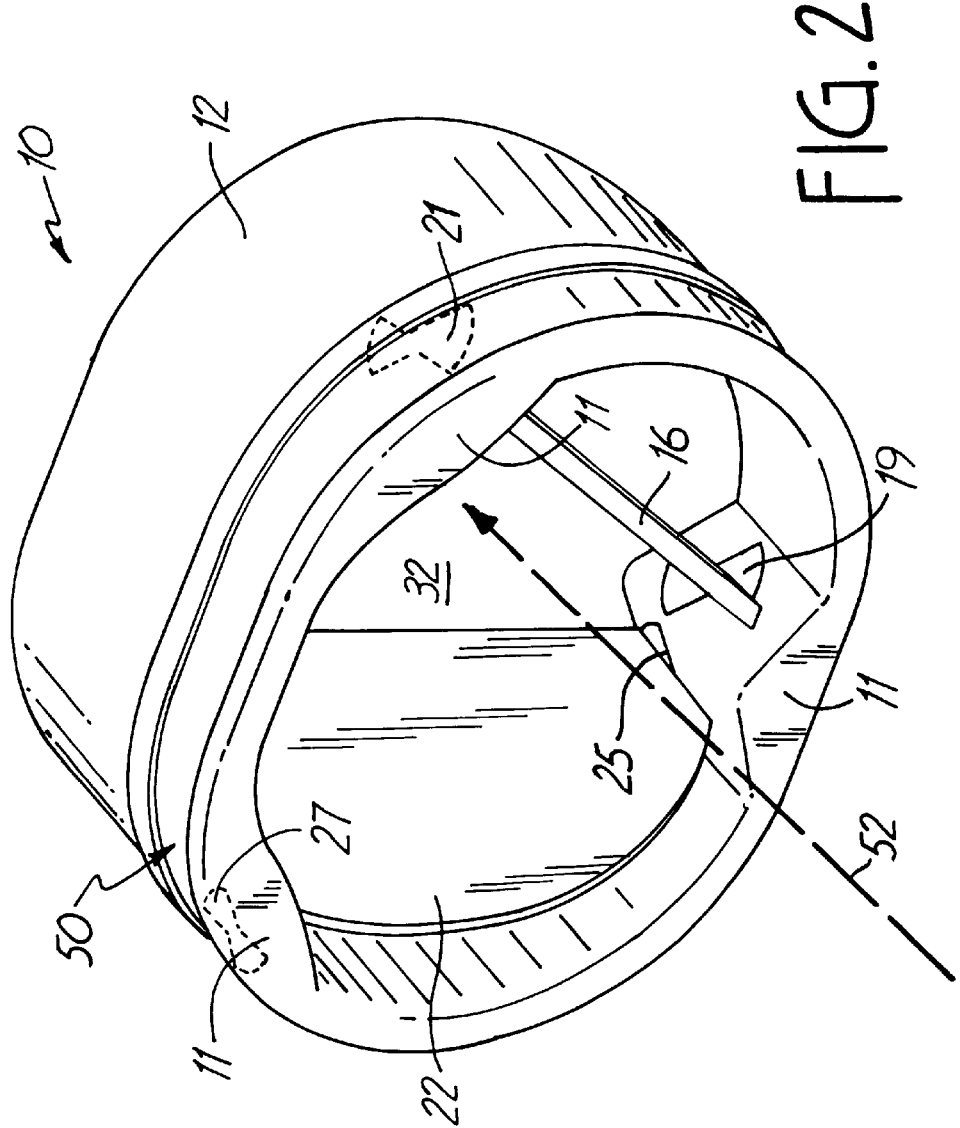
FIG. 2 is a perspective view of the bileaflet heart valve illustrated in FIG. 1A.

For purposes of illustration only, valve 10 is shown as a central opening valve in FIGS. 1A, 1B, 2, 3 and 4. The central opening aspect of the valve 10 is best seen in FIG. 2 which illustrates the direction of blood flow by arrow 52. Blood flow 52 exerts a larger force on the central portions 42 and 46 by virtue of their larger surface area.

As mentioned previously, having the first axis 28 non-parallel to the second axis 30 provides a number of benefits. The non-parallel axes design allows the size of the central opening 32 to be increased while maintaining an efficient use of the orifice area. Increasing the size of the central opening 32 improves the flow and efficiency of the valve 10. The non-parallel axes design also improves the balance between the central 32 and side openings 34 and 36 which increases the flow, decreases the pressure gradient, promotes soft closing and reduces regurgitation.

In addition, the non-parallel axes design permits the valve 10 to be shaped in a number of different geometries in order to better conform to the cardiac anatomy. Better conformance to the cardiac anatomy tends to reduce thrombogenicity and reduce interference between the leaflets 16 and 22 and surrounding cardiac tissue.

Further, because the first 28 and second 30 axes are located closer to the geometric center of the first 16 and second 22 leaflets, respectively, the rotational inertia of the leaflets is decreased and the leaflets open and close gently and smoothly. In particular, assuming the first 16 and second 22 leaflets have a uniform thickness, bringing the axes 28 and 30 closer to the geometric center of the leaflets 16 and 22 better balances the central portions 42 and 46 with the side portions 44 and 48, thereby reducing the rotational inertia. The reduction in rotational inertia reduces the closing impact of the leaflets. The reduction in closing impact, in turn, minimizes the mechanical wear on the pivots 19, 21, 25 and 27 thereby increasing the durability of the valve and making valve operation quieter. The reduction in closing impact also minimizes the probability of blood cell damage. Because the axes 28 and 30 are further from the center edges 38 and 40 as compared to parallel axes valves, the leaflets 16 and 22 react more responsively to subtle hemodynamic changes.

FIG. 2 is a perspective view of the bileaflet heart valve 10 illustrating the position of pivots 19, 21 and 25, 27 which correspond to leaflets 16 and 22, respectively. Each pivot 19, 21, 25 and 27 comprises a protrusion (not visible) extending from the leaflets 16 and 22 into recesses formed in the wall of the housing 12. Those skilled in the art will readily recognize that other pivot designs may be used. The recesses may have stops formed therein to facilitate stopping or limit the rotational movement of the leaflets 16 and 22 between the open and closed positions.

The valve housing 12 preferably includes a means 50 for connection to a suturing cuff (not shown). The suturing cuff facilitates implantation of the valve 10 inside the heart. The connection means 50 may comprise two annular rings extending around the exterior of the housing 12 which define an annular recess therebetween. This type of connection means 50 permits the suturing cuff to be snapped into place. Those skilled in the art will recognize that other connection means may be utilized for the same purpose.

Figure 3:
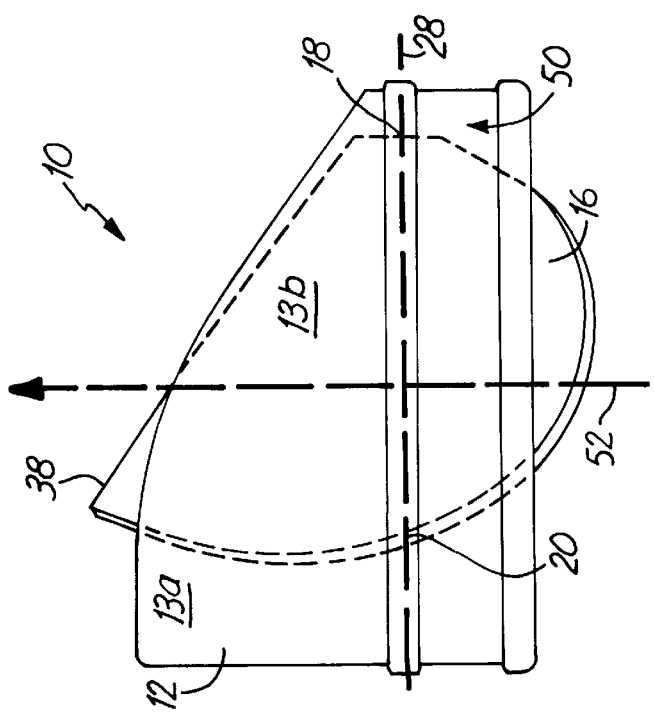
FIG. 3 is a side view of the bileaflet heart valve illustrated in FIG. 1A.

FIG. 3 is a side view of the bileaflet heart valve 10 illustrating the extended portion 13a and 13b of the housing 12. Extended portion 13a substantially protects the upper portion of the leaflets 16 and 22 from interference with the surrounding cardiac tissue when implanted. The reduced profile of extended portion 13b provides more access for blood flow to the coronary ostia in the aortic position. The size and shape of the extended portion 13a,b may be modified depending on the size and shape of the leaflets 16 and 22. In addition, the extended portion 13a,b of the housing 12 may be eliminated if the risk of tissue interference is relatively low.

Figure 4:
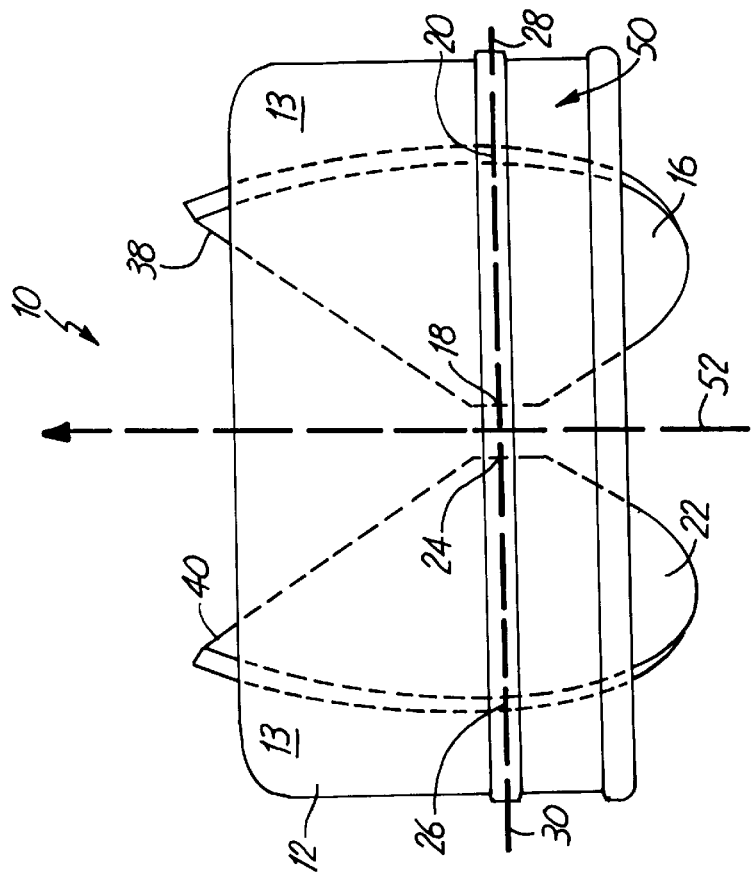
FIG. 4 is a side view of the bileaflet heart valve illustrated in FIG. 3 rotated 90°.

FIG. 4 is a side view of the bileaflet heart valve 10 illustrating the axes 28 and 30 in a co-planar orientation. As mentioned previously, the first 16 and second 22 leaflets are preferably planar, but the leaflets 16 and 22 may be curved or otherwise oriented asymmetrically. The axes 28 and 30 are preferably coplanar but they may be non-coplanar. The leaflets and/or valve body may be arranged in any desired orientation.

FIGS. 5A, 5B, 6A and 6B illustrate various combinations of oval/circular shaped and central/side opening valves 60, 70, 80 and 90. Valve 60 is an oval/side combination, valve 70 is an oval/central combination, valve 80 is a circular/side combination, and valve 90 is a circular/central combination. These various combinations are merely exemplary and those skilled in the art will recognize that other valve shapes may be utilized, depending on the anatomical geometry where the valve is to be implanted. The principles of construction and operation of valves 60, 70, 80 and 90 are substantially the same as valve 10 described previously, except as described hereinafter.

FIG. 5A is a schematic illustration of a side opening oval bileaflet heart valve 60 in the closed position in accordance with another embodiment of the present invention. Bileaflet valve 60 includes first 62 and second 64 leaflets having non-parallel axes of rotation 66 and 68, respectively. The first leaflet 62 has a side portion 63 and a central portion 65. Similarly, the second leaflet 64 has a side portion 67 and a central portion 69. The central portions 65 and 69 have less surface area than the side portions 63 and 67 such that a greater force from the blood flow is exerted on the side portions 63 and 67. Accordingly, the side portions 63 and 67 open in the direction of blood flow and valve 60 may be referred to as a side opening valve.

FIG. 5B is a schematic illustration of a central opening oval bileaflet heart valve 70 in the closed position in accordance with yet another embodiment of the present invention. Bileaflet valve 70 includes first 72 and second 74 leaflets having non-parallel axes of rotation 76 and 78, respectively. The first leaflet 72 has a side portion 73 and a central portion 75. Similarly, the second leaflet 74 has a side portion 77 and a central portion 79. The central portions 75 and 79 have more surface area than the side portions 73 and 77 such that a greater force from the blood flow is exerted on the central portions 75 and 79. Accordingly, the central portions 75 and 79 open in the direction of blood flow and valve 70 may be referred to as a central opening valve.

FIG. 6A is a schematic illustration of a side opening circular bileaflet heart valve 80 in the closed position in accordance with a further embodiment of the present invention. Valve 80 is similar to valve 60 except that valve 80 is substantially circular. Bileaflet valve 80 includes first 82 and second 84 leaflets having non-parallel axes of rotation 86 and 88, respectively. The first leaflet 82 has a side portion 83 and a central portion 85. Similarly, the second leaflet 84 has a side portion 87 and a central portion 89. The central portions 85 and 89 have less surface area than the side portions 83 and 87 such that a greater force from the blood flow is exerted on the side portions 83 and 87 to open the valve. Accordingly, the side portions 83 and 87 open in the direction of blood flow and valve 80 may be referred to as a side opening valve.

FIG. 6B is a schematic illustration of a central opening circular bileaflet heart valve in the closed position in accordance with yet a further embodiment of the present invention. Valve 90 is similar to valve 70 except that valve 90 is substantially circular. Bileaflet valve 90 includes first 92 and second 94 leaflets having non-parallel axes of rotation 96 and 98, respectively. The first leaflet 92 has a side portion 93 and a central portion 95. Similarly, the second leaflet 94 has a side portion 97 and a central portion 99. The central portions 95 and 99 have more surface area than the side portions 93 and 97 such that a greater force from the blood flow is exerted on the central portions 95 and 99. Accordingly, the central portions 95 and 99 open in the direction of blood flow and valve 90 may be referred to as a central opening valve.

FIGS. 7A, 7B and 7C are perspective views of mechanical heart valve prosthesis 110, 120 and 130, respectively, having curved or non-planar leaflets 116, 126 and 136, respectively. Except as described herein with reference to FIGS. 7A, 7B and 7C, all other aspects of valves 110, 120 and 130 are the same as with valve 10.

The curvature of the leaflets 116, 126 and 136 may be concave or convex or a composite of concave and convex portions. The curvature may be two dimensional in one plane or three dimensional in multiple planes. FIG. 7A is a perspective view of a central opening bileaflet heart valve 110 with leaflets 116 having a concave curvature in the plane parallel to the pivot axis in the open position. FIG. 7B is a perspective view of a central opening bileaflet heart valve 120 with leaflets 126 having composite curvature in the plane perpendicular to the pivot axis in the open position. FIG. 7C is a perspective view of a central opening bileaflet heart valve 130 with leaflets 136 having three dimensional composite curvature in the open position.

FIGS. 8A through 12B are illustrations of valve leaflets and valve housing which show various aspects of the invention. In FIG. 8A, leaflets 150 and 152 are shown along with their respective pivot axis. Leaflets 150 and 152 are mounted in housing 154 shown in FIG. BB. FIG. 8A also illustrates pivot points $a_1$, $a_2$, $b_1$ and $b_2$ on the internal surface of the orifice. A pivot axis is provided between points $a_1$ and $b_1$ and between points $a_2$ and $b_2$. FIG. 8B shows the locations of points $a_1$, $a_2$, $b_3$ and $b_2$ relative to housing 154. In the embodiment of FIGS. 8A and 8B, the distance between points $a_1$ and $a_2$ is substantially different than the distance between $b_1$ and $b_2$; in addition, the distance between points $a_1$ and $b_1$ is substantially the same as the distance between $a_2$ and $b_2$ and the two pivot axes are non-parallel but coplanar, as illustrated in FIG. 8B.

In FIGS. 9A and 9B, an embodiment is illustrated in which the distance between points $a_1$ and $a_2$ is substantially different than the distance between $b_1$ and $b_2$; in addition, the distance between points $a_1$ and $b_1$ is different than the distance between $a_2$ and $b_2$ and the two pivot axes are non-parallel and also non-coplanar.

Figure 11B:
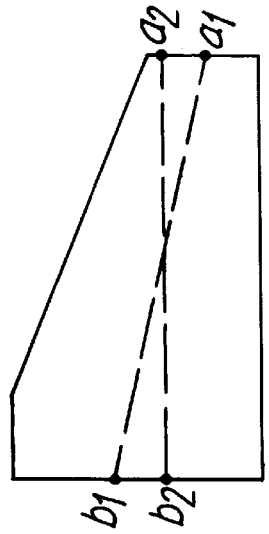
FIG. 11B is a side plan view of a valve illustrating an arrangement of pivot axes in accordance with one embodiment.
Figure 11A:
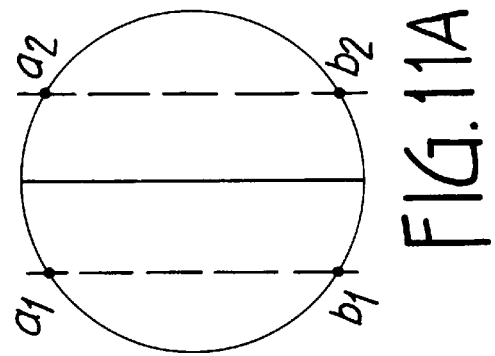
FIG. 11A is a top plan view.

FIGS. 11A and 11B illustrate an embodiment in which the valve axes are co-planar and non-parallel in which the distance between points $a_1$ and $a_2$ is substantially different than the distance between $b_1$ and $b_2$ and the distance between points $a_1$ and $b_1$ is different than the distance between $a_2$ and $b_2$.

Figure 10B:
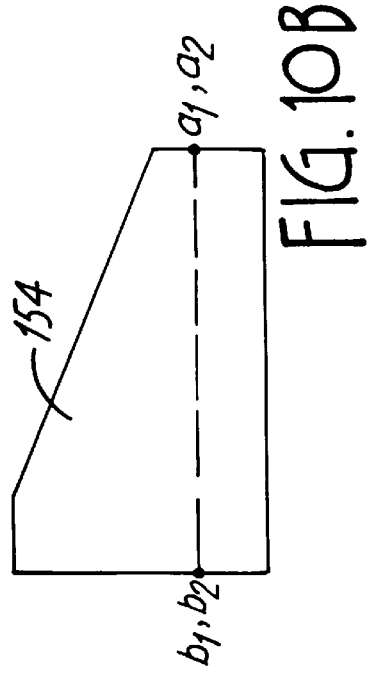
FIG. 10B is a side plan view of a valve illustrating an arrangement of pivot axes in accordance with one embodiment.
Figure 10A:
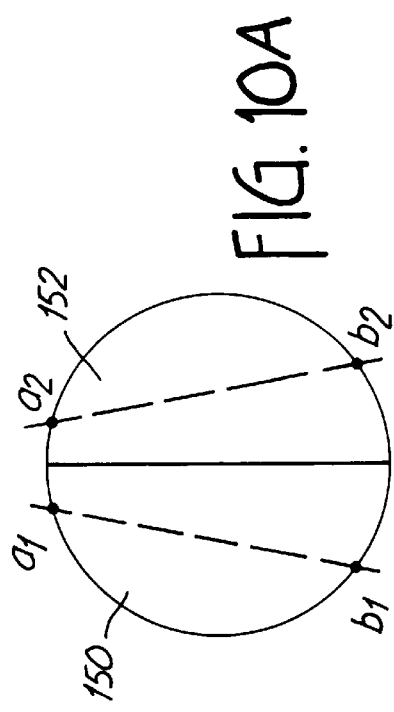
FIG. 10A is a top plan view.

FIGS. 10A and 10B illustrate an embodiment in which the pivot axes are non-coplanar and non-parallel in which the distance between points $a_1$ and $a_2$ is substantially the same as the distance between $b_1$ and $b_2$ and the distance between points $a_1$ and $b_1$ is the same as the distance between $a_2$ and $b_2$.

FIGS. 12A and 12B illustrate an embodiment in which the pivot axes are non-parallel and coplanar and the distance between points $a_1$ and $a_2$ is substantially equal to the distance between $b_1$ and $b_2$ and the distance between points $a_1$ and $b_1$ is different than the distance between $a_2$ and $b_2$.

In the embodiment of FIG. 12A, the pivots are provided using protrusions 156 and recess 158. This may be desirable, for example, if it is believed that flow conditions in the vicinity of one pivot point is different from the flow conditions in the vicinity of the other three pivot points and the differing pivot designs provide a more efficient heart valve.

FIGS. 13A and 13B illustrate an embodiment in which the housing has an irregular shaped orifice and the leaflets 150 and 152 are positioned asymmetrically. This can also provide an embodiment in which the axes are coplanar and non-parallel and the distance between points $a_1$ and $a_2$ is the same as the distance between points $b_1$ and $b_2$.

Although the preceding detailed description sets forth selected preferred embodiments, those skilled in the art will appreciate the scope and spirit of the invention with reference to the appended claims.

What is claimed is:

1. A bileaflet heart valve prosthesis, comprising:

an orifice body defining an orifice for the passage of blood therethrough;

a first occluder disposed in the orifice and pivotally attached to the orifice body, the first occluder pivotally movable about a first axis between an open position and a closed position;

a second occluder disposed in the orifice and pivotally attached to the orifice body, the second occluder pivotally movable about a second axis between an open position and a closed position, the orifice being substantially open when the first and second occluders are in their open positions and substantially closed when the occluders are in their closed positions, the first axis and the second axis being non-parallel.

2. A bileaflet heart valve as in claim 1 wherein the first and second axis form an angle of between about 1 degree and about 179 degrees when projected onto a plane generally perpendicular to the direction of blood flow through the valve.

3. A bileaflet heart valve as in claim 1 wherein the orifice is substantially non-circular.

4. A bileaflet heart valve as in claim 1 wherein the orifice is substantially circular.

5. A bileaflet heart valve as in claim 1 wherein the first axis and the second axis are substantially coplanar.

6. A bileaflet heart valve as in claim 1 wherein the first axis and the second axis are substantially non-coplanar.

7. A bileaflet heart valve as in claim 1 wherein the first and second occluders are planar.

8. A bileaflet heart valve as in claim 1 wherein the first and second occluders are curved.

9. A bileaflet heart valve as in claim 1 wherein each occluder has a central portion that opens in the direction of blood flow through the valve.

10. A bileaflet heart valve as in claim 1 wherein each occluder has a side portion that opens in the direction of blood flow through the valve.

11. A bileaflet heart valve as in claim 1 wherein the valve, when in the open position, defines a central opening and two side openings, the central opening being larger than either of the side openings.

12. A bileaflet heart valve as in claim 1 wherein the valve, when in the open position, defines a central opening and two side openings, the central opening being smaller than either of the side openings.

13. A bileaflet heart valve as in claim 1 wherein the first axis divides the first occluder into a first central area and a first side area, the first central area being greater than the first side area.

14. A bileaflet heart valve as in claim 13 wherein the second axis divides the second occluder into a second central area and a second side area, the second central area being greater than the second side area.

15. A bileaflet heart valve as in claim 1 wherein the first axis divides the first occluder into a first central area and a first side area, the first central area being less than the first side area.

16. A bileaflet heart valve as in claim 15 wherein the second axis divides the second occluder into a second central area and a second side area, the second central area being less than the second side area.

17. A bileaflet heart valve as in claim 1 wherein the orifice body includes an extended portion which extends in an axial direction to prevent the first and second occluder from interfering with surrounding cardiac tissue.

18. The bileaflet heart valve as in claim 17 wherein a portion of the extended portion is tapered to reduce the profile of the valve.

19. A bileaflet heart valve prosthesis, comprising:

an orifice body defining an orifice for the passage of blood therethrough;

a first occluder disposed in the orifice and pivotally attached to the orifice body at opposing pivot points $a_1$ and $b_1$ on an internal surface of the orifice for pivotal movement between an open position and a closed position, a first axis defined by the line connecting points $a_1$ and $b_1$ on the internal surface of the orifice;

a second occluder disposed in the orifice and pivotally attached to the orifice body at opposing pivot points $a_2$ and $b_2$ for pivotal movement between an open position and a closed position, the orifice being substantially open when the first and second occluders are in their open positions and substantially closed when the occluders are in their closed positions, a second axis defined by the line connecting points $a_2$ and $b_2$ on the internal surface of the orifice, wherein the first axis is non-parallel to the second axis.

20. A bileaflet heart valve as in claim 19 wherein the first axis and the second axis are non-coplanar and a distance between $a_1$ and $a_2$ is substantially equal to a distance between $b_1$ and $b_2$.

21. A bileaflet heart valve as in claim 19 wherein the first axis and the second axis are non-coplanar and a distance between $a_1$ and $a_2$ is not equal to a distance between $b_1$ and $b_2$.

22. A bileaflet heart valve as in claim 19 wherein the first axis and the second axis are coplanar and a distance between $a_1$ and $a_2$ is not equal to a distance between $b_1$ and $b_2$.

23. A bileaflet heart valve as in claim 19 wherein the first axis and the second axis are coplanar and a distance between $a_1$ and $a_2$ is substantially equal to a distance between $b_1$ and $b_2$.

24. A bileaflet heart valve as in claim 19 wherein the leaflets are arranged asymmetrically.

25. The bileaflet heart valve as in claim 19 wherein the leaflets are arranged symmetrically.

26. A bileaflet heart valve as in claim 19 wherein a distance between $a_1$ and $b_1$ is substantially equal to a distance between $a_2$ and $b_2$.

27. A bileaflet heart valve as in claim 19 wherein a distance between $a_1$ and $b_1$ is not equal to a distance between $a_2$ and $b_2$.

28. A bileaflet heart valve as in claim 19 wherein the orifice is substantially non-circular.

29. A bileaflet heart valve as in claim 19 wherein the orifice is substantially circular.

30. A bileaflet heart valve as in claim 19 wherein each occluder has a central portion that opens in the direction of blood flow through the valve.

31. A bileaflet heart valve as in claim 19 wherein each occluder has a side portion that opens in the direction of blood flow through the valve.

32. A bileaflet heart valve as in claim 19 wherein the orifice body protects the occluders from interference with surrounding tissue when the valve is in the open position.

33. A bileaflet heart valve as in claim 32 wherein a portion of the orifice body is tapered to reduce valve profile.

* * * * *